United States Patent [19]

Curlee

[11] Patent Number: 4,907,576

[45] Date of Patent: Mar. 13, 1990

[54] ORTHOPAEDIC DEVICE USING NON-STRETCH MATERIAL AND METHOD FOR ITS MANUFACTURE

[76] Inventor: James D. Curlee, 1115 Lisburn Rd. - R.D. 3, Mechanicsburg, Pa. 17055

[21] Appl. No.: 298,423

[22] Filed: Jan. 18, 1989

[51] Int. Cl.⁴ .............................. A61F 5/02; A61F 5/30
[52] U.S. Cl. .......................................... 128/78; 128/69
[58] Field of Search .............................. 128/78, 75, 69

[56] References Cited

U.S. PATENT DOCUMENTS

| | | | |
|---|---|---|---|
| 2,733,712 | 2/1956 | Wuesthoff | 128/78 |
| 2,966,906 | 1/1961 | Wiltrort | 128/75 |
| 3,052,236 | 9/1962 | Schrieber | 128/78 |
| 3,399,669 | 9/1968 | Kaplan | 128/78 |
| 3,400,710 | 9/1968 | Goldstein | 128/78 |
| 3,561,434 | 2/1971 | Kilbey | 128/78 |
| 3,568,670 | 3/1971 | Gaylord, Jr. | 128/78 |
| 3,578,773 | 5/1971 | Schultz | 128/78 |
| 3,605,731 | 9/1971 | Tigges | 128/24 |
| 4,022,197 | 3/1977 | Castiglia | 128/78 |
| 4,159,020 | 6/1979 | von Soiron | 128/78 |
| 4,175,553 | 11/1979 | Rosenberg | 128/75 |
| 4,178,923 | 12/1979 | Curlee | 128/78 |
| 4,627,109 | 12/1986 | Carabelli | 128/78 |
| 4,794,916 | 1/1989 | Porterfield et al. | 128/78 |

FOREIGN PATENT DOCUMENTS 1766250 4/1975 Fed. Rep. of Germany ........ 128/78

Primary Examiner—Edgar S. Burr
Assistant Examiner—Tonya Lamb
Attorney, Agent, or Firm—John S. Roberts, Jr.

[57] ABSTRACT

An orthopaedic belt apparatus applicable to any one of several parts of the body consisting of an elastomeric section sized to encompass lumbar muscle groups of the body wearing the orthopaedic belt and having distal ends thereof, a pair of non-stretch sections of generally rectangular configuration, each section having a first end and a second end, the first end of each section in securement to a distal end of the elastomeric section and the second end of each section sized to be at the front of the body but not meeting the other section's second end when the orthopaedic belt is placed around a portion of the body, a pull strap in selective securement to the second ends of the sections for urging the elastomeric section of the orthopaedic belt into tensioned engagement with the lumbar muscle groups, a foamatitious layer of material interposed between the orthopaedic belt and adjacent body portions, and a three dimensional pad member disposed between the foamatitious layer material and the elastomeric section.

16 Claims, 3 Drawing Sheets

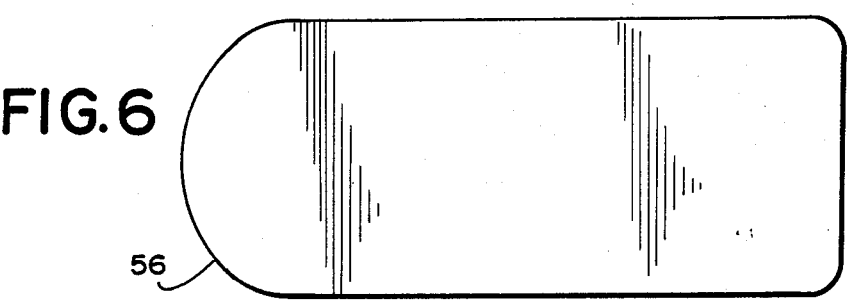
FIG.6
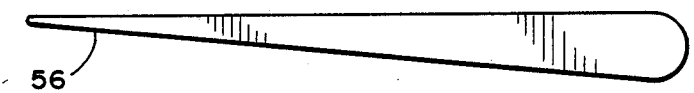
FIG.7
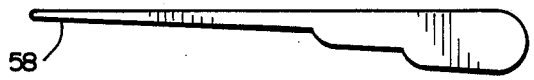
FIG.8
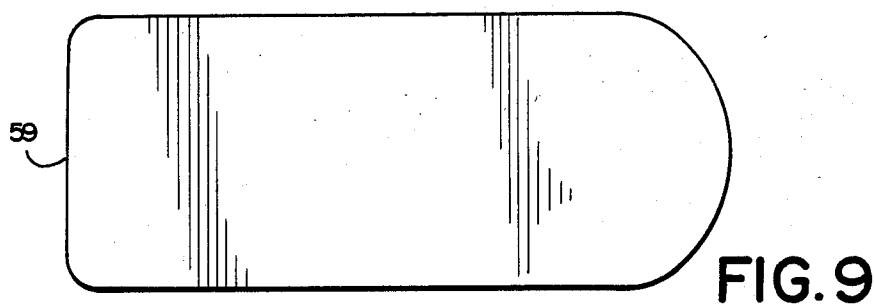
FIG.9
FIG.10
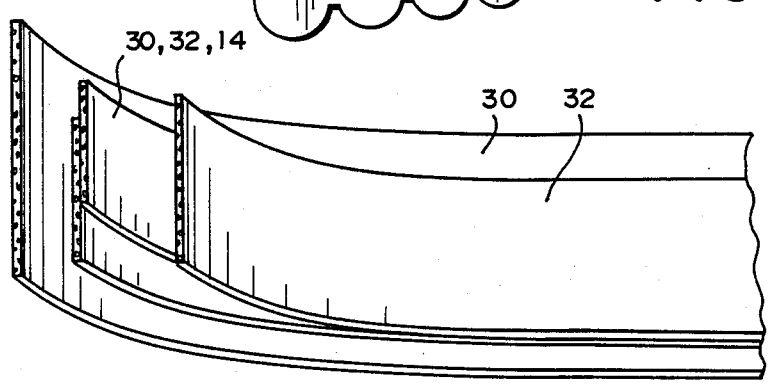
FIG.11
FIG.12

ORTHOPAEDIC DEVICE USING NON-STRETCH MATERIAL AND METHOD FOR ITS MANUFACTURE

BACKGROUND OF THE INVENTION

1. Field of the Invention

The invention relates to an improved orthopaedic device using a non-stretch material in combination with an arrangement of shims or pads and stretch elastic material to generate therapeutic pressure(s) in a specific "foot print" of graduated pressure against muscle tissue and its method for construction thereby, and more particularly, the invention is directed to an orthopaedic belt apparatus applicable to any one of several parts of the body consisting of an elastomeric section sized to entirely encompass lumbar muscle groups of the body wearing the orthopaedic belt and having distal ends thereof, a pair of non-stretch sections of generally rectangular configuration having one end and another end of each of the pair in securement to one respective distal end of the elastomeric section and the other end of each of the pair sized to be foreshortened from their other ends meeting when the orthopaedic belt is placed around a portion of the body, a pull strap means in selective securement to the other ends of the pair of non-stretch sections for urging the elastomeric section of the orthopaedic belt into tensioned engagement with the lumbar muscle groups, a foamatitious layer of material interposed between the orthopaedic belt and adjacent body portions, and a three dimensional pad member disposed between the foamatitious layer material and the elastomeric section.

The belt of the invention is a back support flexible suport device which the wearer pulls into tension with the pull strap connecting both halves of the belt in front of the body of the user. Unstretched, the belt is ideally a few inches shorter than the circumference of the wearer's waist. With sufficient tension to the belt, the stretch elements exert forces against the three dimensional pads, and pressure is generated against the back muscles under the pads in gradient form centrally from the spine outwardly, Greatest pressure concentration is under the thicker sections of the pads and diminishes laterally around the trunk of the user.

The invention relates further to a narrow band or belt device of about ten centimeters width providing for the application of pressure to various parts of the lumbar muscles of the lower back of the body to which it is applied. It could also be constructed in a manner to apply specific patterns of pressure to thigh muscles, to arm muscles and the like.

The device of the invention is a belt which consists of strong layers of stretch material, such as GORE ®, which are tension bands that are located in such a way as to provide tension or stretch support against the lower back, and attached to either end of the stretch material are non-stretch pieces which continue on around the sides of the body and close in front with a pull-strap. GORE is a macroporous fiber or film or may be a membrane which is stetchable; it is available is several grades.

Also incorporated inside the device are two spinae pads in the assembly, which are three dimensional foam pads constructed in such a way that when the belt is properly positioned, these pads lie on either side of the spine, positioned approximately two inches apart, and when the belt is on the body and pulled into tension, the stretch layers, the pads are between the body and the stretch material as one pulls the strap in front of the belt, to create pulled tension on the stretch layers of the GORE ®. The layers of GORE apply tension directly against the pads so positioned on either side of the spine as to put the major portion of counter pressure on the powerful erector spiny muscles which run on or proximate the spine. The pressure begins to diminish by virtue of the construction of the pads as they continue around the side toward the quadratis lumborian, and determines thereby a gradient pattern of pressure going side to side of the spine. The gradient pressure is desirable because one wants most of the pressure on these muscles groups but not the discomfort being cut in half by too much stretch material going the whole way around the body. It is extremely comfortable to wear the support device of the invention over long periods of time because the stretch material is generally confined to an area between 10 and 14 inches across. The non-stretch portion of the belt does not go into tension other than the normal pull of the strap in front, therefore, one does not feel as though the user is cut in half by application of the pressure applied to the user. This is necessary because the therapy that results from the radiant pressure is that of getting the muscles to go from the tight or taut spasmed state into their normal resting length. The therapy is important because it restores full range of motion, the muscles respond normally as opposed to the abnormal tension that they were in which precipitates back strain. Over all, the construction technique for this orthopaedic device which applies therapeutic pressure into a specific area of muscle strain, in this case, the lower back. The result is a very powerful area of counter pressure beneath the twin pads, the twin pads being three dimensionally constructed to direct the downward force of the pressure material and it does not constrict an entire area of the trunk, it is very tolerable to the wearer, does not impair movement and restores normal flexibility within a few minutes of having it on the wearer, thereof as more particularly described herein.

2. Description of the Prior Art

There are devices on the market which have used stretched straps, of various types of elastic material. Various prior art orthopaedic devices, and the like, as well as apparatus and method of their construction in general, are found to be known, and exemplary of the U.S. prior art are the following:

| | |
|---|---|
| Wuesthoff | 2,733,712 |
| Schrieber | 3,052,236 |
| Goldstein | 3,400,710 |
| Gaylord | 3,568,670 |
| Tigges | 3,605,731 |
| Castiglia | 4,022,197 |
| von Soiron | 4,159,020 |
| Curlee | 4,178,923 |
| Carabelli | 4,627,109 |

Schrieber and Goldstein disclose belts having elastic and non-flexible areas. Schrieber also provides for a support pad adjacent the spinal area and Goldstein uses VELCRO ® as a fastening member. Curlee further discloses VELCRO fasteners and includes inflatable support pads adjacent the spinal area, as does Tigges.

Wuesthoff, Carabelli and Castiglia generally show support means including a belt of elastic material and a VELCRO fastener in the lumbro sacral area on sides lateral of the back bone. Gaylord discloses an elastic belt having a cushioned pad support member.

These patents or known prior uses teach and disclose various types of orthopaedic devices of sorts and of various manufactures and the like as well as methods of their construction, but none of them whether taken singly or in combination disclose the specific details of the combination of the invention in such a way as to bear upon the claims of the present invention.

SUMMARY OF THE INVENTION

An object, advantage and feature of the invention is to provide a novel belt and orthopaedic device that provide the positioning, the layering and the construction technique for the flexible support device that reduces the constricting aspect of being bound by long lengths of elastic band. It is quite different having the flexible support of the invention on which controls the area of elasticity, it is different from having a totally elastic corset or brace around the trunk which simply encases the body like a sausage or the like. For comfort's sake, the non-stretch ends attach to the middle area which is the stretch layered GORE are slipped inside a SPANDEX sleeve which is attached close to the very ends of the belt on either end. The effect of that is the belt is allowed to elongate and to significantly alter their position as the GORE stretches for tension.

Another object of the invention is to provide a device that is not an overly wide like a corset, but is merely about 10 cm. in width, the same allowable for olympic weight lifting belts, and it utilizes powerful, overlapping layers of stretch-bands under which are twin 3-dimensional spinae pads; powerful support pressure is generated in a precise zone across the entire lumbar area; because the pressure is gradient, highest concentration is atop the massive erector spinae group and gradually diminishes around the sides over the quadratus lumborium; and all the back muscles receive stimulus and therefore are in no way weakened by the belt.

Another object of the invention is to provide a flexible support belt combining elastic and non-elastic members into a strong structure that is effective to provide strength to the body portions affected.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWINGS

FIG. 6 is a plan view and FIG. 7 is a side view of a gradient lumbar pressure wedge as used in the belt of the invention.

FIG. 8 is side view of a modified wedge that is used in the belt.

FIG. 9 is a plan view and FIG. 10 is a side view of a another gradient lumbar pressure wedge as used in the belt of the invention.

FIG. 11 is a side view of another wedge of the belt of the invention.

FIG. 12 is an isometric or perspective view of one stacking of material for an arrangement of strips of stretch elastic, such as GORE, as used in the invention.

DESCRIPTION OF A PREFERRED EMBODIMENT OF THE INVENTION

Figure 1:
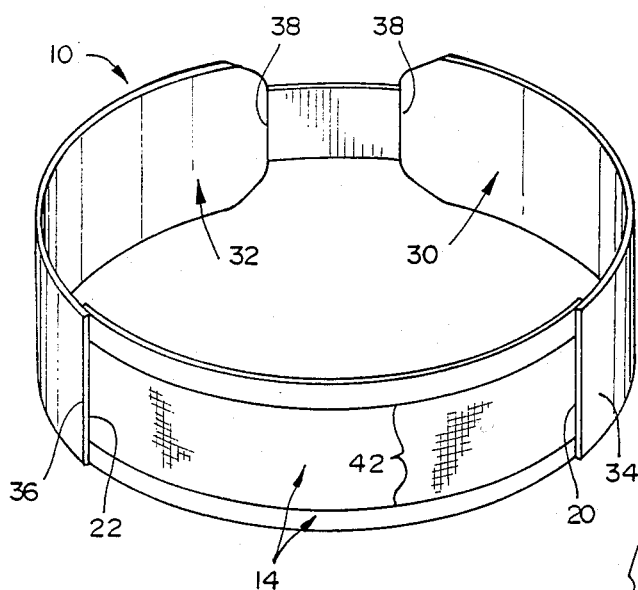
FIG. 1 is a perspective view of an orthopaedic device using non-stretch materials of the invention and illustrating a typical installation of the belt according to a preferred embodiment and best mode of the present invention.
Figure 2:
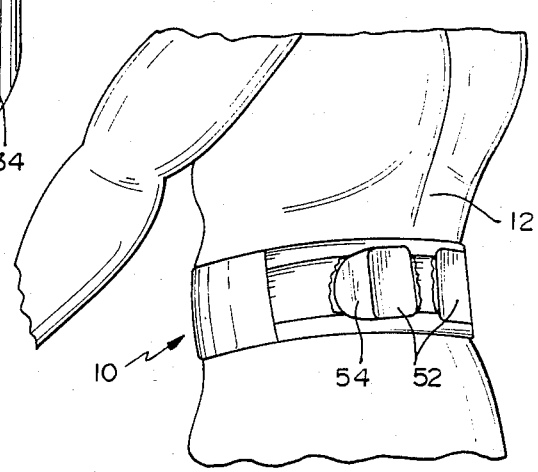
FIG. 2 is a prspective view of the belt being worn as shown and embodying the concepts of the invention.
Figure 3:
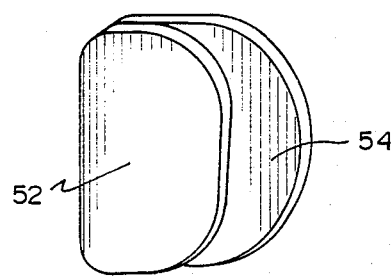
FIG. 3 is a perspective view of a set of spinae pads of the invention.
Figure 4:
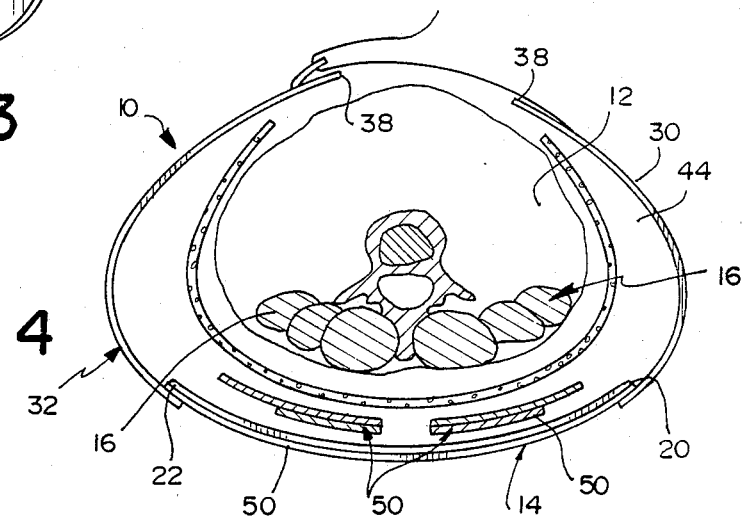
FIG. 4 is a sectional view of a body of a user to which the belt is applied according to a preferred embodiment of the invention.
Figure 5:
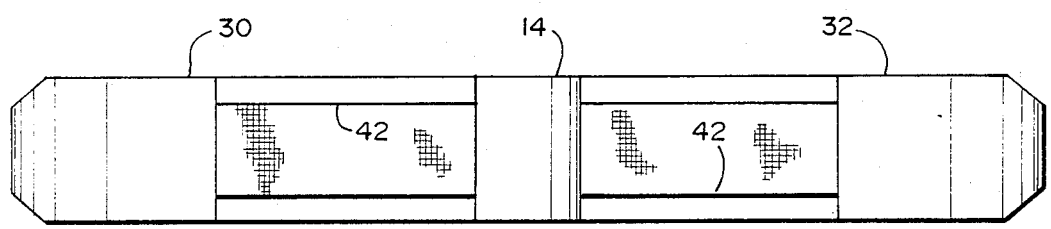
FIG. 5 is a plan view of an alternative arrangement of the belt of the invention with stretch and non-stretch materials of the invention.
Figure 1A:
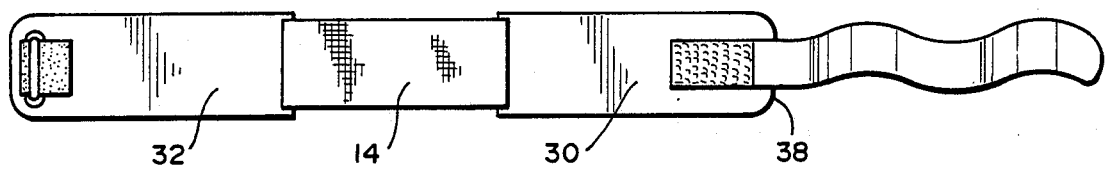
FIG. 1A is a plan view of the belt showing the elastic and the non-stretch sections.
Figure 2A:
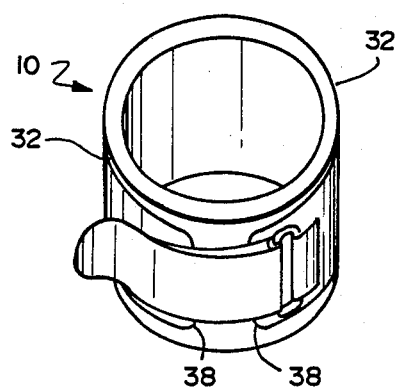
FIG. 2A is a perspective view of the belt with the pull strap engaged.
Figure 3A:
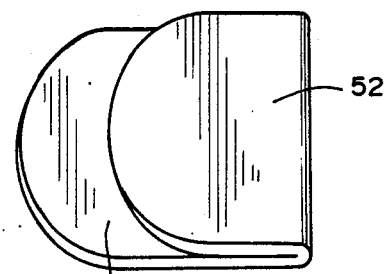
FIGS. 3A through 3D show additional embodiments of the wedge.
Figure 3C:
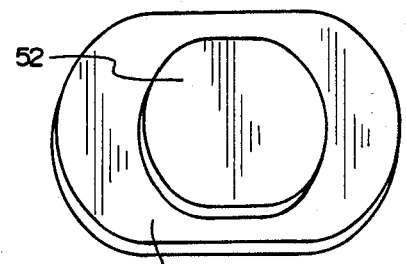
Figure 3B:
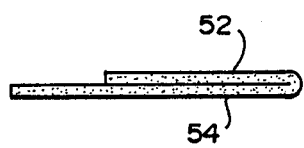
Figure 3D:
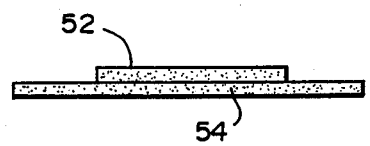
Figure 5A:
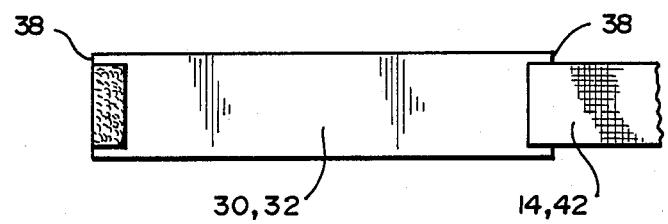
FIG. 5A is an enlarged view of a non-stretch section.

Referring now to the drawings there is shown in FIG. 1 an orthopaedic belt 10 applicable to any one of several parts of the body 12 shown in FIGS. 2 and 4, an elastomeric section 14 sized to entirely encompass lumbar muscle groups 16, 18 of the body wearing the orthopaedic belt 10 and the elastomeric section 14 having distal ends 20, 22 thereof shown connected to a pair of non-stretch sections 30, 32 of a generally rectangular configuration having one end 36 and another end 38 of each of the pair in securement to one respective distal ends 20, 22 of the elastomeric section 14 and the other end of each of the pair sized to be foreshortened from their other ends meeting at a pull strap 40 when the orthopaedic belt is placed around a portion of the body. The elastomeric section includes at least one of several longitudinal seams 42, 42 for directing stresses and strains as they may function for focussing these forces along the seams 42, 42.

The pull strap 40 is in selective securement to the other ends 38, 38 of the pair of non-stretch sections 30, 32 for urging the elastomeric section 14 of the orthopaedic belt 10 into tensioned engagement with the lumbar muscle groups 16, 18.

Shown in FIG. 4 is a foamatitious layer 44 of material interposed between the orthopaedic belt 10 and adjacent body portions thereof, and three dimensional pads 50 disposed between the foamatitious layer material 44 and the elastomeric section 14. Insertable into these areas of pads are also spinae pads 52, 54 of FIGS. 3A through 3D; spinae pads 56, 58 of FIGS. 6-8; spinae pads 59 of FIGS. 9 and 10; and spinae pads 60 of FIG. 11. The three dimensional pad means are displacably insertable in relative securement into the othopaedic belt 10, and the three dimension pad 50-60 are variously and selectively configured to effect various effects of pressure, tension, and impact on the lumbar muscles of the user.

The orthopaedic device of the invention uses non-stretch material in combination with stretch elastic to generate therapeutic pressure in a specific "foot print" of graduated pressure against muscle tissue, and the device of the invention is applicable to any of several parts of the body. Muscle tissue responds to mechanical pressure applied at specific pressure points by releasing its contracted state. Frequently called trigger points, these areas have been recognized for centuries among so-called accupressure or accupuncture therapists. In modern times, physical therapists, athletic trainers and doctors have applied pressure by hand to coax tight muscles into a relaxed state. This mechanical release of muscle tension has significant therapeutic benifits: it halts pain due to spasms in the back or thigh, for example; it makes bending and lifting on the job less of a task or hazard for the individual who is likely to suffer a muscle tear when tight muscle fibers resist elongation; and tight, spasmed muscles do not heal as rapidly from "soft tissue damage" as quickly as they might in a relaxed state.

Typical muscle strain occurs when a worker or athlete moves in such a way as to demand elongation or stretch of certain muscle groups. Bending low to pick up an object from the floor is a good example of back muscles being stretehed long to allow the body to bend forward. Tight muscle fibers must be "pulled" or forced to stretch. Often the individual moves faster than the muscles allow and a forced or ballistic stretch that tears individual fibers. A muscle spasm is an involuntary contraction of muscle tissue and it restricts normal flexibility. In very chronic patients, involuntary contractions occur at frequent times during activities which put the individual at risk of serious muscle damage such as a dock worker would experience during work routines of lifting, bending, and twisting. A common method of eliminating muscle spasms is to administer powerful muscle-relaxing drugs. This is not always practical and in many cases the side effects are dangerous.

The belt device of the invention relaxes muscle tightness, spasms and contractions, without the need for these powerful drugs and it is capable of being worn around the waist to provide constant relaxing pressure for low back muscles. As long as sufficient pressure is generated by the device against the back muscles, spasms do not return. The wearer is given complete freedom and range of motion without restriction. The belt device of the invention assures proper attainment of pressure against the specific muscle groups without causing the wearer any discomforture and provides for the replaceable stretch elements thereof being confined to a restricted region of the back. Extending from either side of the elastic elements are non-elastic belt pieces which wrap around the sides of the trunk and abdomen which allows use of very elastic elements without the entire belt seemingly "cutting" the wearer in half. The non-elastic portions of the belt absorb pull against the sides and front of the body and dissipate pressures at very tolerable levels.

Varying widths and stacking arrangements, such as shown in the drawings including FIG. 12, of elastic stretch fabrics or material or elements known as GORE, are situated across the lumbar region of the back and ride atop the pair of three dimensional spinae pads 50–60. GORE is a macroporous fiber or film, sometimes described as a membrane which is rigid but stretchable and comes in several grades of material, including its main grade. The pads are located on a floating sleeve or strip in the assembly of the belt 10 and place themselves approximately one inch on either side of the spinal column. Each pad covers a major group of back muscles and as shown in the FIGS. 6–11 are stepped in thickness and shape to thus provide pressure in graduated form. The pressure is greater immediately to the right and left of the spine and diminishes gradually around to the sides of the body. This arrangement of pads 50–60 and stacked GORE place maximum pressure where it is needed most to relax tight muscle tissue and prevent excess constriction of the trunk which would otherwise become intolerable to the wearer in a short period of time. The devices of the invention are actuated by pulling a single strap through a slip ring and attaching the end of the strap to VELCRO securement members. Various degrees of tension may be applied to the back simply by pulling or releasing the strap. The belt is 10 cm, forming a narrow construction, yet provides constriction of broad areas of the trunk.

The apparatus of the orthopaedic belt 10 of the invention may be so constructed and arranged in its component parts that it may be assembled as a kit or in kit form.

The foregoing is considered as illustrative only of the principles of the invention. Further, since numerous modifications and changes will readily occur in those skilled in the art, it is not desired to limit the invention to the exact construction and operation shown and described, and accordingly, all suitable modifications and equivalents may be resorted to falling within the scope of the invention.

What is claimed and desired to be secured by Letters Patent is:

1. An orthopaedic belt for generating graduated pressure against the lumbar muscle groups comprising
   an elastomeric section sized to encompass said muscle groups and having distal ends thereof,
   a pair of non-stretch sections of generally rectangular configuration, each section having a first end and a second end, the first end of each section in securement to a distal end of the elastomeric section and the second end of each section sized to be at the front of the body but not meeting the other section's second end when the orthopaedic belt is placed around a portion of the body,
   a pull strap means in selective securement to the second ends of the sections for urging the elastomeric section of the orthopaedic belt into tensioned engagement with the lumbar muscle groups,
   a foamatitious layer of material interposed between the orthopaedic belt and adjacent body portions,
   three dimensional pad means disposed between the foamatitious layer material and the elastomeric section,
   the three dimensional pad means being contoured for developing and generating pressure against said lumbar muscle groups, and
   the elastomeric section including at least one longitudinal seam for directing stress and strain functions of said pressure along the seam,
   wherein a further non-stretch section is interposed between distal ends of the elastomeric section.

2. The apparatus of claim 1 wherein the three dimensional pad means are contoured and configured with a straight edge on one side thereof and a contoured edge oppositely disposed thereto to purpose a decrease in pressure toward the contoured edge.

3. The apparatus of claim 1 wherein the three dimensional pad means are displacably insertable in relative securement to the orthopaedic belt.

4. The apparatus of claim 1 wherein the the three dimensional pad means is of foamed plastic and is in relative securement to the orthopaedic belt.

5. The apparatus of claim 1 wherein the width dimension of the orthopaedic belt is of a uniform value throughout the length of the orthopaedic belt.

6. The apparatus of claim 1 wherein the second end portions of the orthopaedic belt have VELCRO ® fastener means.

7. The apparatus of claim 1 wherein the elastomeric material is GORE ®.

8. The apparatus of claim 1 wherein the three dimensional pad means is configured to form a stepped array.

9. Method of making an orthopaedic belt for generating graduated pressure against the lumbar muscle groups comprising the steps of forming an elastomeric section sized to encompass said lumbar muscle groups and having distal ends thereof, configuring a pair of non-stretch sections of generally rectangular shape, each section having a first end and a second end, placing the first end of each section in securement with a distal end of the elastomeric section and sizing the second end of each section to be at the front of the body but not meeting the other section's second end when the orthopaedic belt is placed around a portion of the body, securing a pull strap means to the second ends of the sections for urging the elastomeric section of the orthopaedic belt into tensioned engagement with the lumbar muscle groups, interposing a foamatitious layer of material between the orthopaedic belt and adjacent body portions, disposing three dimensional pad means between the foamatitious layer material and the elastomeric section, contouring said three dimensional pad means for developing and generating pressure agains the lumbar muscle groups, including at least one longitudinal seam in the elastomeric section for directing stress and strain functions of said pressure along the seam, and including a further non-stretch section interposed between distal ends of the elastomeric section.

10. The apparatus of claim 9 wherein the three dimensional pad means are contoured and configured with a straight edge on one side thereof and a contoured edge oppositely disposed thereto to purpose a decrease in pressure toward the contoured edge.

11. The method of claim 9 wherein the three dimensional pad means is in relative securement to the orthopaedic belt.

12. The method of claim 9 wherein the the three dimensional pad means is of foamed plastic and is in relative securement to the orthopaedic belt.

13. The method of claim 9 wherein the width dimension of the orthopaedic belt is of a uniform value throughout the length of the orthopaedic belt.

14. The method of claim 9 wherein the second ends of the orthopaedic belt have VELCRO ® fastener means.

15. The method of claim 9 wherein the elastomeric material is GORE ®.

16. The method of claim 9 wherein the three dimensional pad means is configured to form a stepped array.

* * * * *